US011833360B2

(12) United States Patent
Kotlarchik et al.

(10) Patent No.: US 11,833,360 B2
(45) Date of Patent: Dec. 5, 2023

(54) CARRY PACK FOR A WEARABLE CARDIOVERTER DEFIBRILLATOR

(71) Applicant: WEST AFFUM HOLDINGS DAC, Dublin (IE)

(72) Inventors: Garrett M. Kotlarchik, Kenmore, WA (US); Kiah Lesher, SEattle, WA (US); Phillip D. Foshee, Jr., Woodinville, WA (US); Daniel J. Finney, Woodinville, WA (US); David P. Finch, Bothell, WA (US)

(73) Assignee: West Affum Holdings DAC, Dublin (IE)

( * ) Notice: Subject to any disclaimer, the term of this patent is extended or adjusted under 35 U.S.C. 154(b) by 336 days.

(21) Appl. No.: 16/425,864

(22) Filed: May 29, 2019

(65) Prior Publication Data

US 2019/0366110 A1    Dec. 5, 2019

Related U.S. Application Data

(60) Provisional application No. 62/677,566, filed on May 29, 2018.

(51) Int. Cl.
*A61N 1/39* (2006.01)
(52) U.S. Cl.
CPC ......... *A61N 1/3968* (2013.01); *A61N 1/3904* (2017.08)
(58) Field of Classification Search
CPC ................ A61N 1/3968; A61N 1/3904; A45F 2005/006; A45F 2005/1013;
(Continued)

(56) References Cited

U.S. PATENT DOCUMENTS 3,724,355 A    4/1973 Busch et al.
4,411,267 A *  10/1983 Heyman .............. A61B 5/0006
                                                       224/663
(Continued)

FOREIGN PATENT DOCUMENTS

DE    2005060985 A2    6/2007
EP       2305110 A1    4/2011
(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.

(Continued)

*Primary Examiner* — Gary Jackson
*Assistant Examiner* — Alexander M Eisenberg
(74) *Attorney, Agent, or Firm* — Christensen O'Connor Johnson Kindness PLLC

(57) ABSTRACT

In one embodiment, a carrying case for a wearable cardioverter defibrillator (WCD) is described. The carrying case includes a container with a front wall, a rear wall, and a gusset coupling the front wall and the rear wall. The carrying case also includes each of the front wall and rear wall including multiple fabric layers. The carrying case also includes two connection points inset from an edge of the rear wall. The carrying case also includes an adjustable strap removably coupled to the connection points, the adjustable strap configured to be worn in various configurations on a body of a patient.

22 Claims, 15 Drawing Sheets

(58) Field of Classification Search
CPC .......... A45F 2003/007; A45F 2003/008; A45F 2003/002; A45F 3/02

See application file for complete search history.

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,666,432 A | 5/1987 | McNeish et al. | |
| 4,698,848 A | 10/1987 | Buckley | |
| 4,757,804 A * | 7/1988 | Griffith | A61N 2/02 600/13 |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,577,652 A * | 11/1996 | Cooper | A45F 3/02 224/153 |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,765,735 A * | 6/1998 | Kimchi | A45F 3/12 224/264 |
| 5,782,878 A | 7/1998 | Morgan et al. | |
| 5,792,204 A | 8/1998 | Snell | |
| 5,887,777 A * | 3/1999 | Myles | G06F 1/163 190/102 |
| 5,902,249 A | 5/1999 | Lyster | |
| 5,913,685 A | 6/1999 | Hutchins | |
| 5,944,669 A | 8/1999 | Kaib | |
| 5,960,952 A * | 10/1999 | Chen | A45C 13/36 190/125 |
| 6,047,203 A | 4/2000 | Sackner et al. | |
| 6,065,154 A * | 5/2000 | Hulings | A61N 1/3904 2/102 |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 * | 8/2001 | Glegyak | A61N 1/3904 607/5 |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,109,421 B2 * | 2/2012 | McLean | A45C 13/30 224/655 |
| 8,135,462 B2 | 3/2012 | Owen et al. | |
| 8,140,154 B2 | 3/2012 | Donnelly et al. | |
| 8,369,944 B2 | 2/2013 | Macho et al. | |
| D680,324 S * | 4/2013 | Phillips | D3/218 |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,265,432 B2 | 2/2016 | Warren et al. | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 2001/0027834 A1 * | 10/2001 | Southwick | A45F 5/00 150/108 |
| 2002/0162872 A1 * | 11/2002 | Cascioli | A45F 5/00 224/637 |
| 2002/0181680 A1 | 12/2002 | Linder et al. | |
| 2003/0158593 A1 | 8/2003 | Heilman et al. | |
| 2004/0148108 A1 * | 7/2004 | Irish | A61M 39/18 702/31 |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0223892 A1 * | 9/2008 | Hamilton | A45F 5/00 224/267 |
| 2008/0312709 A1 | 12/2008 | Vollpe et al. | |
| 2009/0005827 A1 | 1/2009 | Weintraub et al. | |
| 2009/0057188 A1 * | 3/2009 | Kroll | A45C 11/00 206/569 |
| 2010/0007413 A1 | 1/2010 | Herleikson | |
| 2010/0193559 A1 * | 8/2010 | Van Huyssteen | A63B 57/60 224/680 |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 * | 6/2012 | Guldalian | A61N 1/0484 2/102 |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 * | 9/2013 | Kaib | G16H 40/63 607/5 |
| 2013/0245388 A1 | 9/2013 | Rafferty et al. | |
| 2013/0274565 A1 | 10/2013 | Langer et al. | |

(56) References Cited

U.S. PATENT DOCUMENTS

| | | |
|---|---|---|
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0303460 A1* | 10/2014 | Corley ............... A61B 5/0205 600/301 |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0270728 A1* | 9/2015 | Williams ............. H02J 7/0044 320/111 |
| 2015/0297135 A1 | 10/2015 | Shoshani et al. |
| 2015/0297904 A1* | 10/2015 | Kavounas ........... A61B 5/6843 607/6 |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0166321 A1* | 6/2016 | Amsler ................ B23P 19/04 607/5 |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0246466 A1* | 8/2017 | Murphy ............... A61N 1/3904 |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | | | |
|---|---|---|---|---|
| JP | 4320257 A | 3/2005 | | |
| JP | 5963767 A | 1/2014 | | |
| JP | 2014526282 A | 10/2014 | | |
| WO | 98/39061 A2 | 9/1998 | | |
| WO | 1998039061 A2 | 9/1998 | | |
| WO | 2011/146448 A1 | 11/2011 | | |
| WO | 2012/064604 A1 | 5/2012 | | |
| WO | 2012064604 A1 | 5/2012 | | |
| WO | WO 2012063196 A1 * | 5/2012 | ........... | A61N 1/3968 |
| WO | 2012/151160 A1 | 11/2012 | | |
| WO | 2015/056262 A1 | 4/2015 | | |

OTHER PUBLICATIONS

Heartstart MRx and XL AED Algorithm—Application Note, Jul. 2001, Edition 2 Phillips Healthcare, USA.

Zoll LifeVest Model 4000 Patient Manual PN 20B0047 Rev B, (C) 2009-2012.

LifeVest wearable defibrillator, 2 pages, 2015 ZOLL Medical Corporation, United States.

Adler, New Drugs and Technologies, Wearable Cardioverter-Defibrillators, Article, 2013 American Heart Association, Inc, pp. 854-860, Tel Aviv University, Tel Aviv, Israel.

ZOLL LifeVest images, website with images, 2019 ZOLL Medical Corporation, https://lifevest.zoll.com/news/imagery, 4 pages.

Heartstart MRx and XL AED Algorithm—Application Note, Jul. 2001, Edition 2 Philips Healthcare, USA.

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

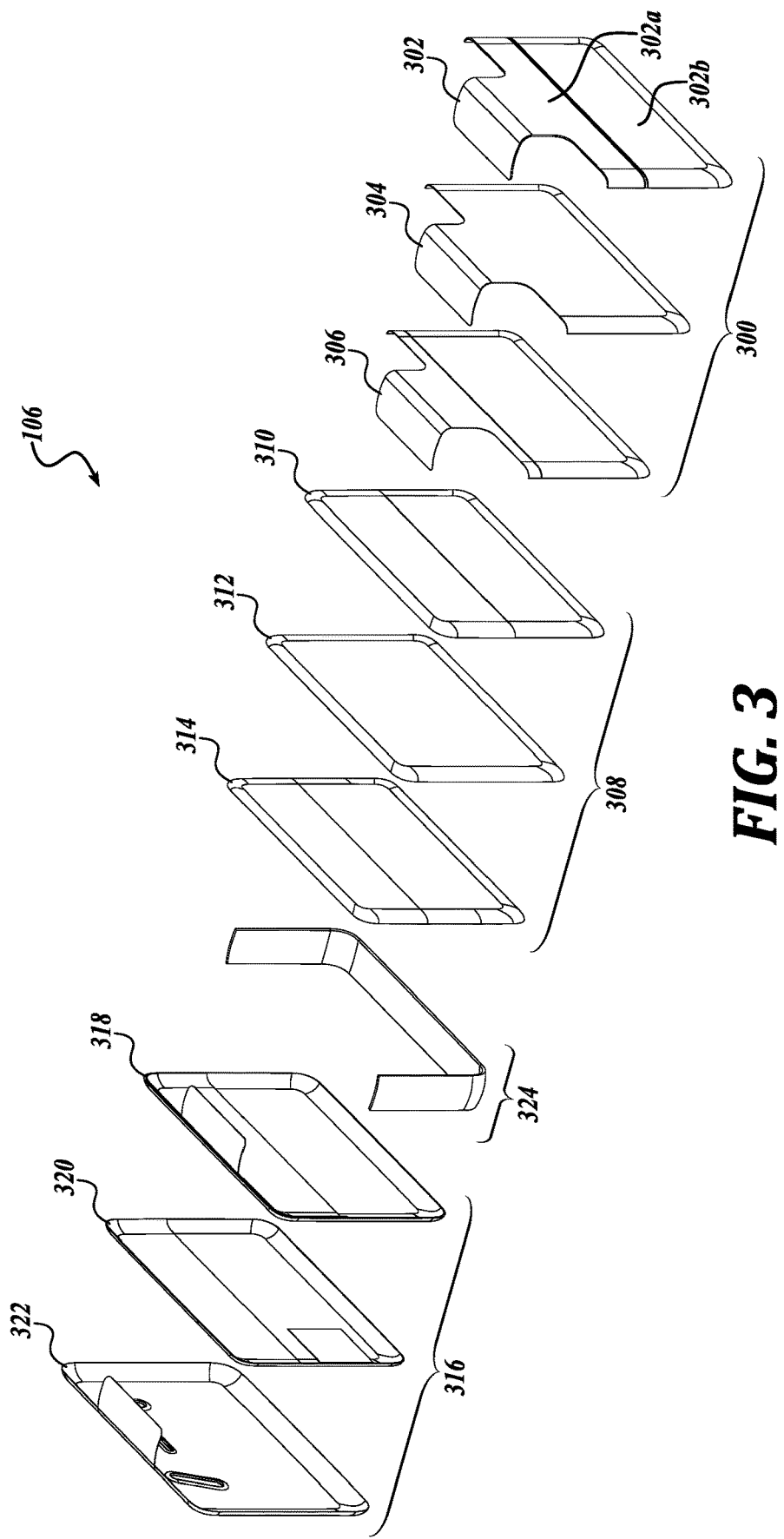

CARRY PACK FOR A WEARABLE CARDIOVERTER DEFIBRILLATOR

CROSS-REFERENCE TO RELATED APPLICATION

This application claims the benefit of U.S. Provisional Application No. 62/677,566 filed May 29, 2018, the disclosure of which is hereby incorporated by reference herein in its entirety for all purposes.

BACKGROUND

Heart arrhythmias may reduce blood flow to various parts of the body. In some instances, arrhythmias results in a Sudden Cardiac Arrest (SCA) where a person's heart suddenly and unexpectedly stops beating. If this occurs, blood may stop flowing to the brain and other vital organs. SCA can lead to death very quickly, within minutes, unless action is taken quickly.

Some people have an increased risk of SCA. This includes people who have had a heart attack, a prior SCA episode, among other risk factors. Frequently, these people are recommended for an Implantable Cardioverter Defibrillator ("ICD"). The ICD is a small electronic device connected to the heart that continuously monitors the person's electrocardiogram ("ECG"). If or when the ICD detects certain types of heart arrhythmias or abnormalities, then the ICD delivers an electric pulse or shock to the heart.

A patient may have a period of time between being recommended for an ICD and actually receiving one. In the interim timeframe, a patient may be suited with a wearable cardioverter defibrillator ("WCD") system. A WCD system is worn by the patient and includes, among other components, a defibrillator and one or more external electrodes. When a patient wears a WCD system, the WCD may monitor several patient parameters, including the patient's ECG. If a potentially life threatening arrhythmia is detected, the defibrillator may be activated and primed to deliver an appropriate electric shock through the patient's body which also shocks the heart.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, a carrying case for a wearable cardioverter defibrillator (WCD) is described. The carrying case includes a container with a front wall, a rear wall, and a gusset that couples the front wall to the rear wall. The front wall and rear wall both include multiple fabric layers. Two connection points are inset from an edge of the rear wall. The carrying case also includes an adjustable strap removably coupled to the connection points, and the adjustable strap is configured to be worn in various configurations on a body of a patient.

In further embodiments, the adjustable strap may include a first adjustable section and a second adjustable section. The carrying case may also include a pocket formed on the front wall of the container. The carrying case may also include one or more straps coupled to the rear wall, the straps configured to hold one or more wires. The carrying case may also include a handle coupled to the rear wall. A latching strap may retain a defibrillator in the container. The carrying case may also include one or more adjustable cinchers coupled to the strap. The one or more adjustable cinchers may have a rubber coating. In some embodiments, a quick release coupling attached to the strap. The quick release coupling may have a rubber coating. In some embodiments, a belt clip coupled to the back wall.

In another embodiment, a WCD system is described. The WCD system includes a defibrillator housing. A discharge circuit is in communication with the defibrillator housing, the discharge circuit configured to discharge a stored electrical charge through a body of the patient. A processor is positioned within the defibrillator housing, the processor in communication with the discharge circuit. The WCD system includes a carrying case with a container to hold the defibrillator housing. The carrying case has a front wall, a rear wall, and a gusset coupling the front wall and the rear wall and forming the container. The carrying case also includes each of the front wall and rear wall including multiple fabric layers. The carrying case also includes two connection points inset from an edge of the rear wall. The carrying case also includes an adjustable strap removably coupled to the connection points, the adjustable strap configured to be worn in various configurations on a body of a patient.

In another embodiment, a carrying case for a wearable cardioverter defibrillator is described. The carrying case includes a container with a front wall, a rear wall, and a gusset that couples the front wall to the rear wall. The carrying case also includes each of the front wall and rear wall including multiple fabric layers. The carrying case also includes two connection points inset from an edge of the rear wall. The carrying case also includes an adjustable strap removably coupled to the connection points, the adjustable strap configured to be worn in various configurations on a body of a patient. The carrying case also includes a pocket formed on the front wall of the container. The carrying case also includes one or more straps coupled to the rear wall, the straps configured to hold one or more wires. The carrying case also includes one or more adjustable cinchers coupled to the strap. The carrying case also includes a quick release coupling attached to the strap.

DESCRIPTION OF THE DRAWINGS

FIG. 3 is an exploded view of the exemplary carrying pack shown in FIGS. 2A-2B.

DETAILED DESCRIPTION

Figure 1:
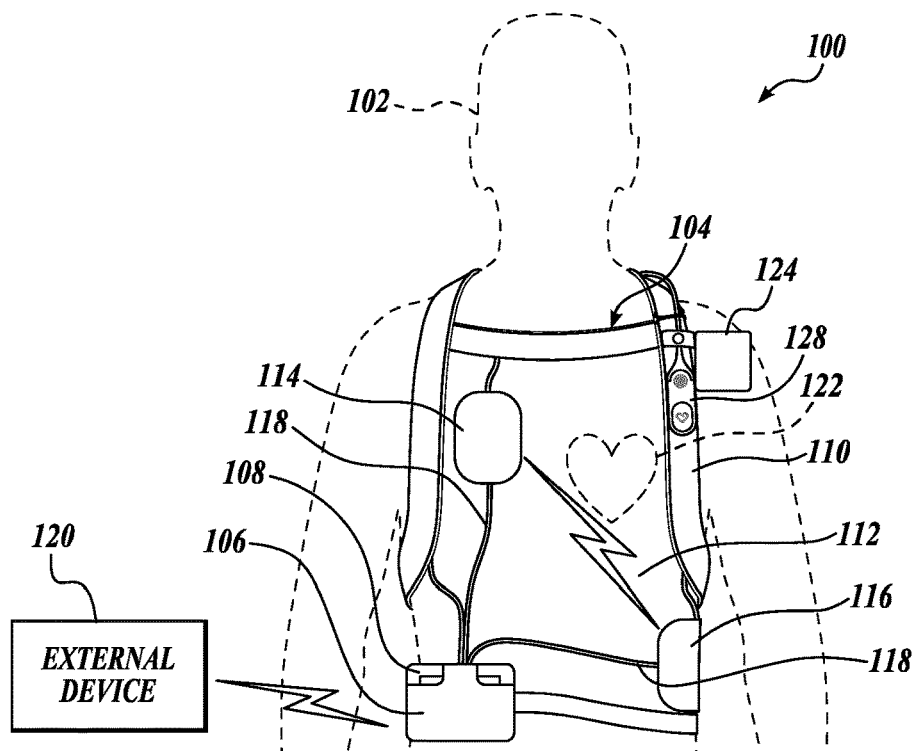
FIG. 1 is a diagram of a sample WCD system in accordance with the present disclosure.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest (SCA). A patient at risk for SCA are expected to wear or keep the defibrillator in close proximity to their bodies for twenty-four (24) hours a day up to ninety (90) days. That's 2,160 total hours of continuous use. To help patients comply with this request, the carrying pack of the defibrillator must be comfortable but also practical to allow the patient to easily engage with and review the components of the WCD. Therefore, the carrying case of the defibrillator needs to be comfortable, but also allow the patient to access the defibrillator One of the most important characteristics for a pack to be comfortable while wearing it for such a lengthly time is the ability for the patient to wear the pack in different parts of the body as one position becomes uncomfortable over time or as the patient changes activities. Additionally, people generally have different preferences for where and how they wear packs. The carrying case disclosed herein provides the patient with various positions and styles to wear components of the WCD to ensure the patient continues to use and wear the WCD system.

Previous packs have limited wearability. Typically, they can be worn either over the shoulder or on a belt via a clip. However, the clip design for waste wear is flimsy and does not provide a stable carrying position. The pack flops about as the patient goes about daily activities and can be difficult for people with poor hand mobility to use. Additionally, previous packs are difficult to connect and disconnect the pack's strap.

The pack described in this embodiment provides a carrying case that allows for the patient to wear the pack comfortably on their waist and over their shoulder. The carrying case includes a strap with two adjustable sections. Each section has a strap a length adjuster. The first length adjuster may include a tri-glide that can adjust its strap from a first length to a second length. The second length adjuster may include a free end strap section adjusted by a friction buckle that can be adjusted from a very short first length to a longer length. The carrying case also may include a quick disconnect buckle near the pack that enables it to be quickly and securely taken on and off.

The adjustability of the strap enables the carrying case to hug the patient's body and remain stable during movement. The carrying case insets the connection points in from the outer edge of the pack. As a person's body is roundish shaped, if the straps are attached to the outside of a flat object, the flat object will cause it to rotate and wobble around the body. By insetting the connection points, the strap and the carrying case does not wobble about the body as it is being carrying in such a position.

The carrying case described herein softens features normally hard or potentially rough surfaces which had potentially led to patient discomfort. The carrying case incorporates a rubber coating on the hardware including the snaps, belt clip, D-rings, and tri-glide. The rubber coating makes them softer to the touch, warmer against the skin, and prevents noisy metal on metal clanking noises.

The strap of the carrying pack uses soft nylon webbing for the strap. The nylon webbing provides a comfortable surface that rests against skin. To further increase comfort, the construction of the carrying case hides the attachment of the belt clip and D-rings behind the main body fabric. Therefore, the surface that rests against the patient's skin is smooth.

Referring now to FIG. 1, a system 100 with a patient 102 wearing an example of a WCD system 104 according to embodiments described herein is illustrated. The WCD system may include a support structure 110, a carrying case 106 holding an external defibrillator 108 connected to defibrillation electrodes 114, 116, among other components.

The support structure 110 may be worn by the patient 102. The support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. For example, the support structure 110 may also include a carrying case 106 to hold components of the WCD system 104 including the defibrillator 108. In some embodiments, the carrying case 106 may be carried via a shoulder, around a waist of the patient 102 or may be kept close to the patient 102 such as in a cart, bag, stroller, wheel chair, or other vehicle.

The external defibrillator 108 may be coupled to the support structure 110 or may be carried remotely from the patient 102. The external defibrillator 108 may be triggered to deliver an electric shock to the patient 102 when patient 102 wears WCD system 104. For example, if certain thresholds are exceeded or met, the external defibrillator 108 may be engaged and deliver a shock to the patient 102.

The WCD system 104 may defibrillate the patient 102 by delivering an electrical charge to the patient 102 through a series of electrodes 114, 116 positioned on the torso 112. The electrodes 114, 116 may be electrically coupled to the external defibrillator 108 via a series of electrode leads 118. The defibrillator 108 may administer an electric shock to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116. The electric shock may be a defibrillation shock, which may go through a heart 122 of the patient 102 in an attempt to restart the heart 122. The brief, strong electric pulse may work to restart the heart 122 which may save the patient's life.

Figure 2A:
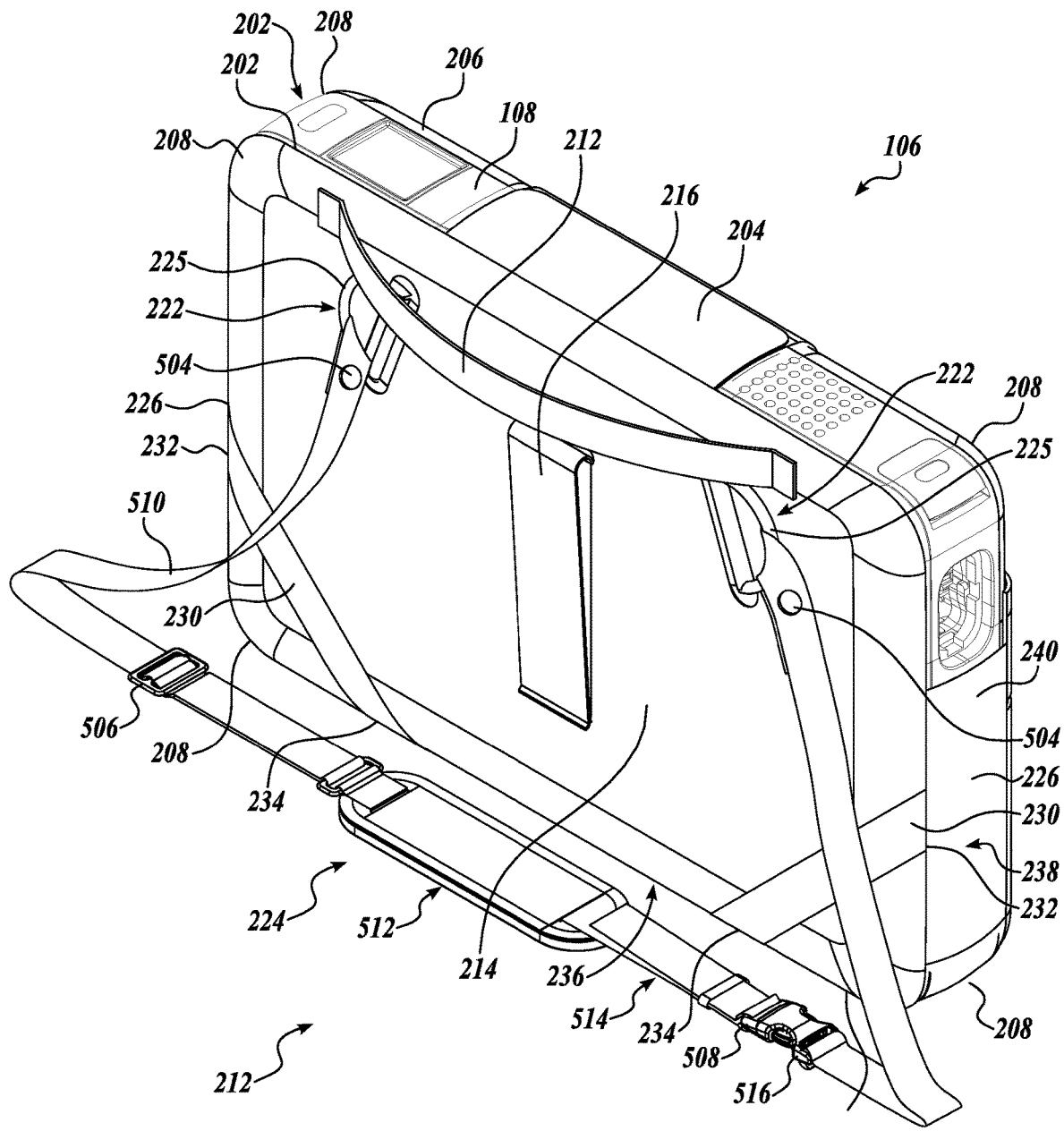
FIGS. 2A-2B are various isometric views of an exemplary carrying pack for a WCD shown in FIG. 1.
Figure 2B:
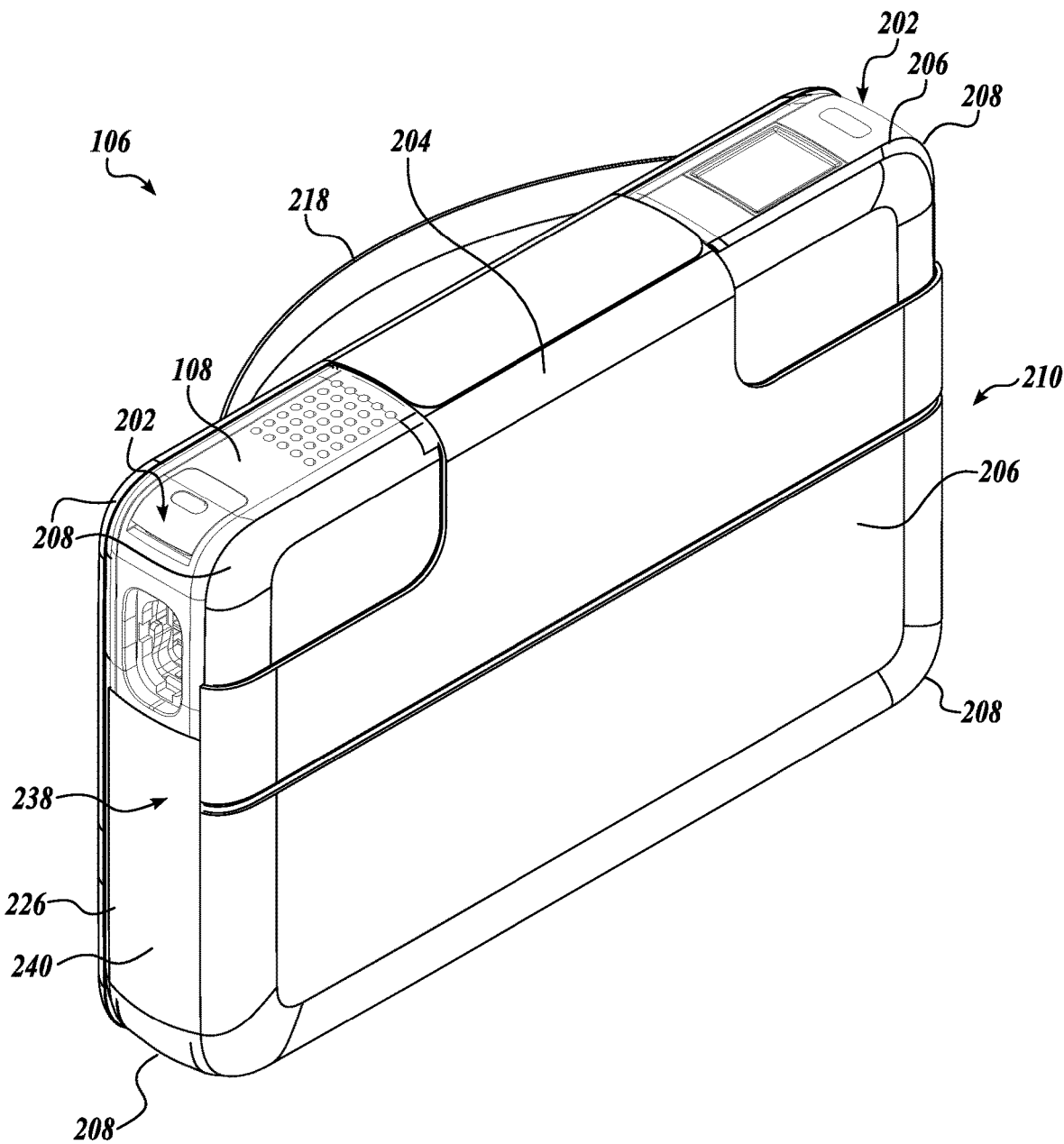

FIGS. 2A-2B are isometric views of the carrying case 106 according to one or more embodiments described herein. The carrying case 106 may hold the defibrillator 108 component of the WCD system 104 and enable the patient to comfortably keep the defibrillator 108 within reach to increase patient compliance wearing the WCD system. The case 106 may include an opening 202 to accept the defibrillator 108.

Referring to FIGS. 2A and 2B, the carrying case 106 may have a rectangular shape with rounded corners 208 to match the shape of the defibrillator 108. The case 106 can be adapted to any shape to meet multiple defibrillators 108 depending upon the WCD system. For example, the carrying case 106 can be squarish, larger, smaller, or the like. The carrying case 106 may have an opening 202 to accept the defibrillator 108. A latching strap 204 may secure the defibrillator 108 into the carrying case 106. The latching strap 204 may couple to the bag using snaps, hook and loop closure, buckles, or the like. In some embodiments, a patient may request a carrying case 106 with a latching system that is easiest for them to use. For example, elderly patients may prefer to use a hook and loop closure system whereas a person with more dexterity may prefer the snap, button, or buckle closure.

The latching strap 204 enables a user carry the defibrillator 108 but also view the communication screen, access buttons, and speakers of the defibrillator 108. Likewise, carrying case 106 allows the patient to position the defibrillator 108 such that the screen of the defibrillator 108 may be viewed on either side of the latching strap 204. For example, a right-handed patient may hold the carrying case 106 on their right side and want the screen more visible on the left side of the pack. In other embodiments, a patient may wear the carrying case 106 on their left side and have the screen on a right side to interact with the defibrillator 108.

As shown in FIG. 2A, in some embodiments, a rear side 214 of the carrying case 106 may include a belt clip 216. The belt clip 216 may attach to a patient's waistband or belt to secure the carrying case 106 to the patient's torso. A strap 224 may also be used in this carrying configuration to retain the case 106 in a more secure position around the patient's waist.

The strap 224 may connect to the rear side 214 of the carrying case 106 at two connection points 222 for connecting a larger strap 224 to the carrying case 106. The connection points 222 may be set in from an edge 226 of the carrying case 106. This may allow the carrying case 106 and the strap 224 to better wrap the bag around a person's waist. For example, by being inset from an edge 226 of the case 106, the strap 224 not try to wrap a flat object around the waist. Instead, the flat portion of the case 106 that contacts the patient's waist is reduce and, coupled with the belt clip, provides a more secure mountain mounting location and a more comfortable wearing configuration.

In some embodiments, the connection points 222 may include two D-rings 225 or other fasteners to couple to the strap 224. In some embodiments, the strap 224 may be removable from the carrying case 106. For example, the strap 224 may have a release mechanism 504 such as snaps, hook and loop, buckles, or other closure types to removably couple to the connection points 222.

In some embodiments, a handle 212 may be located on a rear side 214 of the carrying case 106. The handle 212 may enable the patient to interact with and easily carry the carrying case 106 without using the strap 224.

In some embodiments, the carrying case 106 may include one or more wire straps 230. The wire straps 230 may be positioned in the corner of the carrying case 106. The straps 230 may reach across the rear 214 of the carrying case 106 from a first point 232 on the edge 226 of the carrying case 106 to a second point 234 on a bottom 236 of the carrying case 106. The straps 230 may comprise an elastic material such that the straps 230 may put a tension on any item placed between the strap 230 and the rear side 214 of the carrying case 106. The straps 230 may hold wires or other cords and items associated with the WCD device 104. The straps 230 may hold loose wires from hanging around and getting caught on items or otherwise affected.

As shown in both FIGS. 2A and 2B, in some embodiments, the side 238 of the carrying case 106 includes a gusset 240 that does not extend the full height of the carrying case 106. Instead, the gusset 240 ends short of the full height of the carrying case 106 to allow easier access to the defibrillator 108 and to put the defibrillator in and out of the carrying case 106. The gusset 240 also widens the width of the carrying case 106 and provides structural stability to the case 106.

Referring now to FIG. 2B, a front 210 of the carrying case 106 may include a pocket 206. The pocket 206 may be positioned to easily accept the patient's personal items such as keys, mobile devices, instructions, emergency notes, and the like. In some embodiments, the pocket 206 may have a closure such as a zipper, hook and loop, button, buckle, or snap enclosure or may be an open pocket. The pocket 206 may enable the patient to easily access items in the stored away.

FIG. 3 is an exploded view of the different layers of the carrying case 106. As can be seen, each portion of the case 106 has multiple layers of material for each different section. The pocket 300 has three main layers 302, 304, 306, with the first layer 302 comprising two layers, 302-a, 302-b to form the front pocket. The front panel 308 has three layers 310, 312, 314. The back panel 316 has three layers 318, 320, 322 with the middle layer 320 having three layers condensed into it. The gusset 324 has a single layer.

Figure 4:
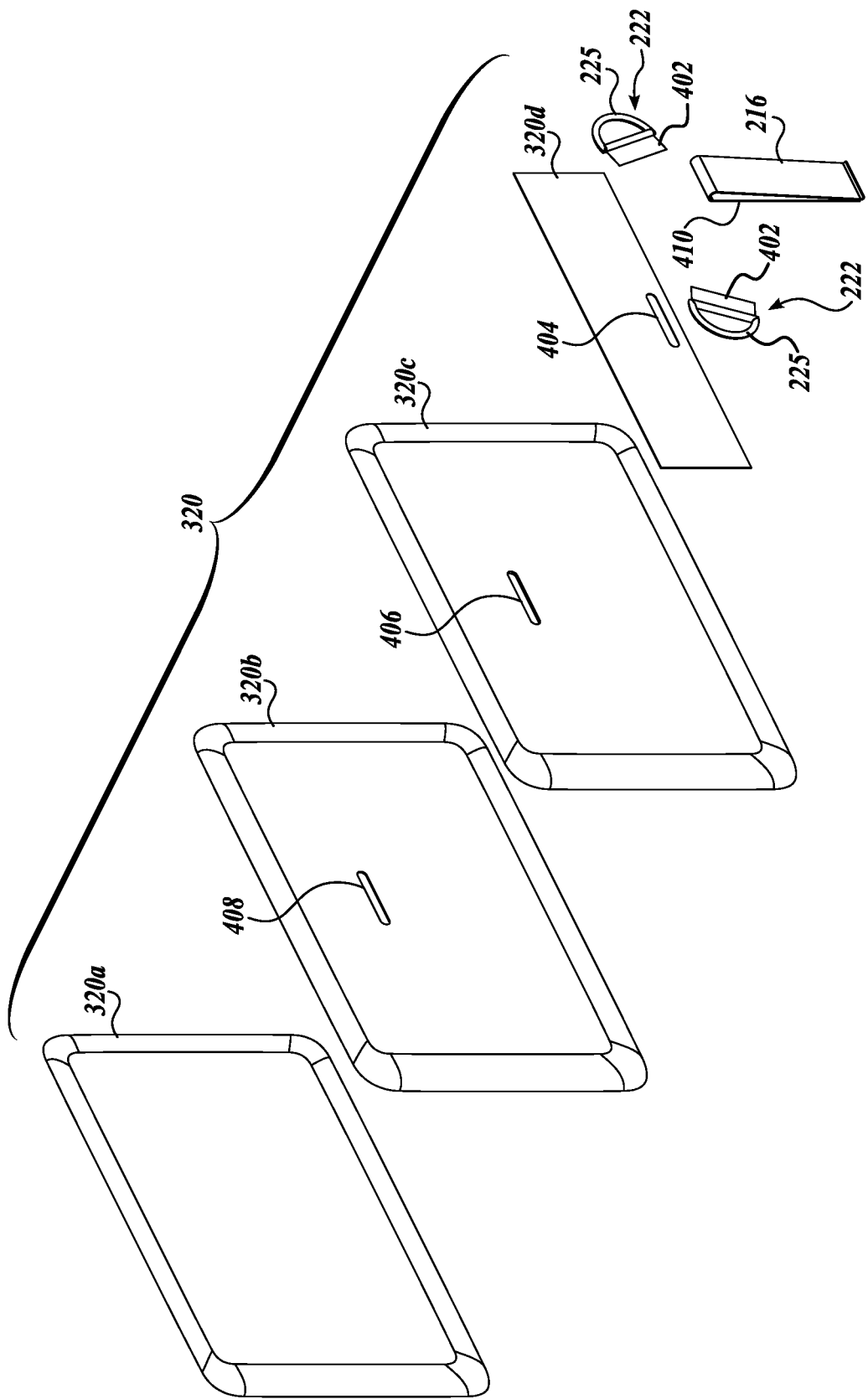
FIG. 4 is an exploded rear-view of the exemplary carrying pack shown in FIGS. 2A-2B.

FIG. 4 is an exploded view of the rear layer 320 with the connection point 222 and belt clip 216 shown. The connection points 222 may include a D-ring 225 and tacking fabric 402. The tacking fabric 402 may couple the D-rings 225 to the rear layer 320 of the pack 106. As shown, to enforce the connection points 222, the tacking fabric 402 may be sewn into all of the layers 320-a, 320-b, 320-c, 320-d. A rear portion 410 of the belt clip 216 may be inserted into openings 404, 406, 408 in the first layers 320d, 320c, 320b before all the layers 320a, 320b, 320c, 320d are adhered together. This type of construction of the layer 320 may securely couple the connection points 222 and belt clip 216 to the layer 320 while also providing padding to prevent the stitching or other components from pressing against the patient.

Figure 5:
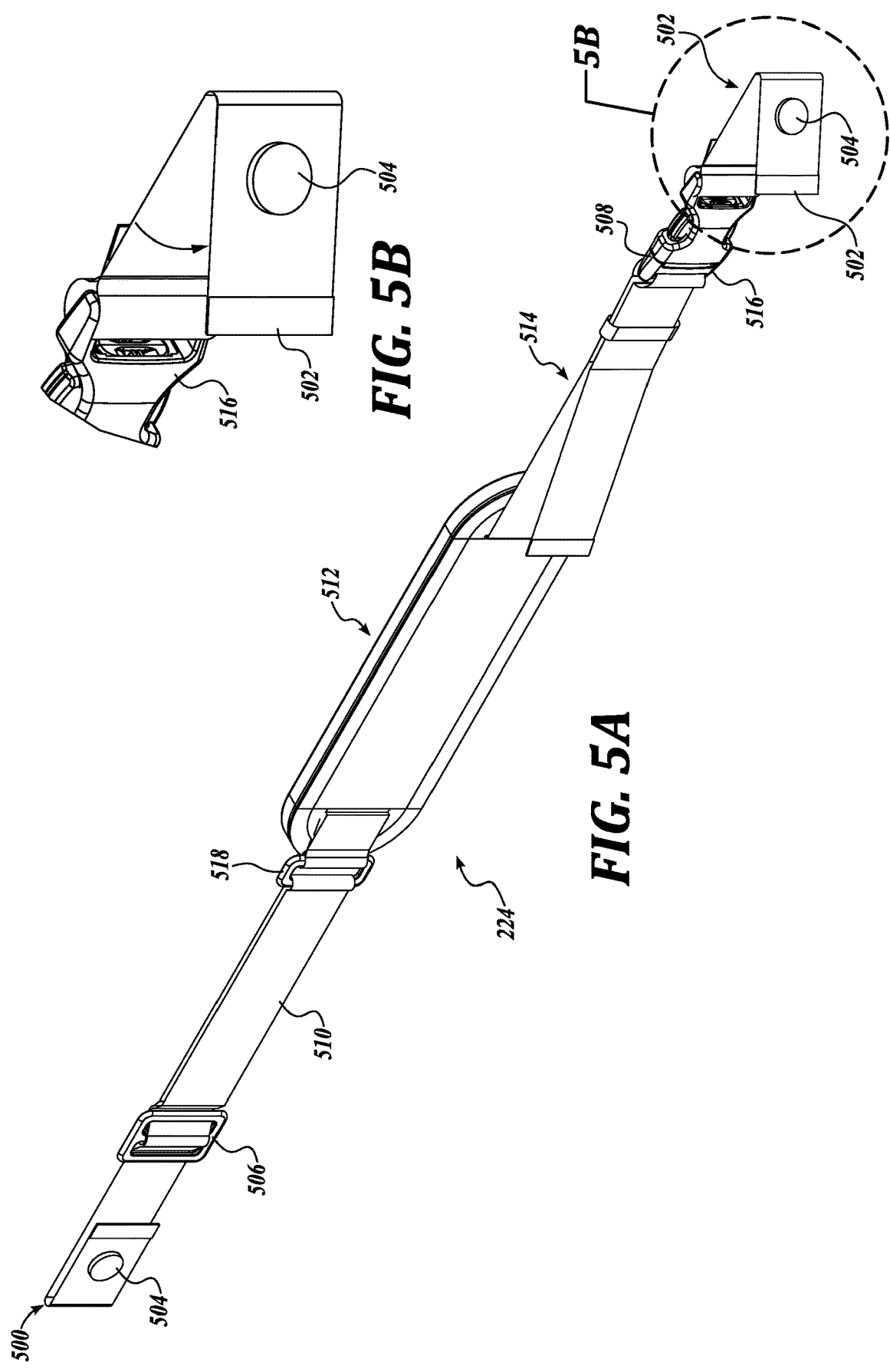
FIG. 5A is an isometric view of the carrying strap of the exemplary carrying pack shown in FIGS. 2A-2B.
FIG. 5B is an detailed view of the carrying strap of the exemplary carrying pack shown in FIGS. 2A-2B.

FIG. 5A is a schematic of the strap 224 shown in FIG. 2A. As can be seen in FIG. 5A, the strap 224 has a first end 500 that removably couples to a connection point (e.g. connection point 222) and a second end 502 opposite the first end 500 that removably couples to a second connection point (e.g. connection point 222). The strap 224 as shown has snaps 504 to removably couple the strap 224 to the connection points 222. For example, as shown in FIG. 5B, the end 502 of the strap 224 may fold over (and around connection point) and couple to itself using snaps 504. However, the strap 224 may incorporate hook and loop closure, buckles, a cinch connection point, a double D-ring connection, or the like.

Referring back to FIG. 5A, in some embodiments, the strap 224 may have one or more strap adjusters 506, 508. The strap adjusters 506, 508 may enable the strap 224 to expand or contract from a first length, L1, to a second length, L2, and anywhere in between. A first portion 510 of the strap 224 may connect to the connection point on the pack 106 and extend to a padded portion 512 of the strap 224. In some embodiments, the first portion 510 may connect to a loop ring 518 which may connect to padded portion 512.

In some embodiments, a second portion 514 of the strap 224 may connect to an opposite side of the padded portion 512 and extend to the second strap adjuster 508. The strap adjuster 508 may be an independent component or may be a part of a quick release buckle 516. The quick release buckle 516 may enable the patient to quickly remove and/or place the carrying case 106 in any carrying position.

Figure 6:
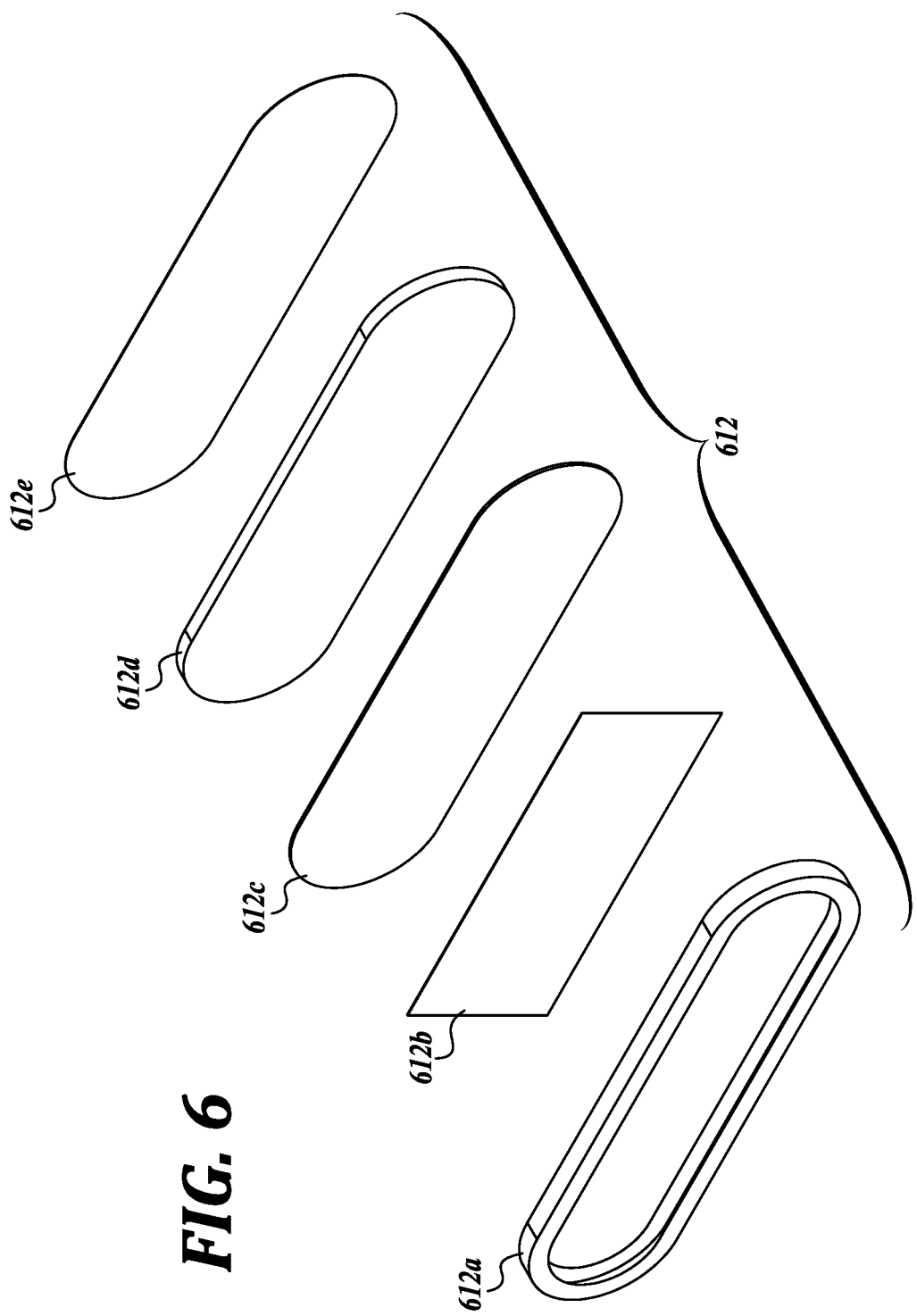
FIG. 6 is an exploded view of the carrying strap cushion of the exemplary carrying pack shown in FIGS. 2A-2B.

FIG. 6 shows an exploded view of the various layers 612-a, 612-b, 612-c, 612-d, 612-e of the padded portion 612. The layers 612-b, 612-c, 612-d, 612-e provide maximum comfort to the patient while in use. The top most layer 612-b may provide a passageway for the strap 224 to loop through the padded portion 612 and retain the padded portion 612 on a section of the strap 224. Layer 612-a may hold layers 612-b, 612-c, 612-d, 612-e together.

The strap adjusters 506, 508 may enable the patient to wear the pack 106 in multiple configurations to maximize comfort and therefore conformance. The pack 106 may be worn as a cross-body bag, a waist bag, a simple over the strap, and the like. The ability for the pack 106 to expand and contract enables the patient to change the position of the pack 106 to maximize comfort and change positions throughout the day to match the patient's activities. Furthermore, because the strap 224 is removable, the patient can customize the lengths of the strap 224 to match their body shape.

Figure 7:
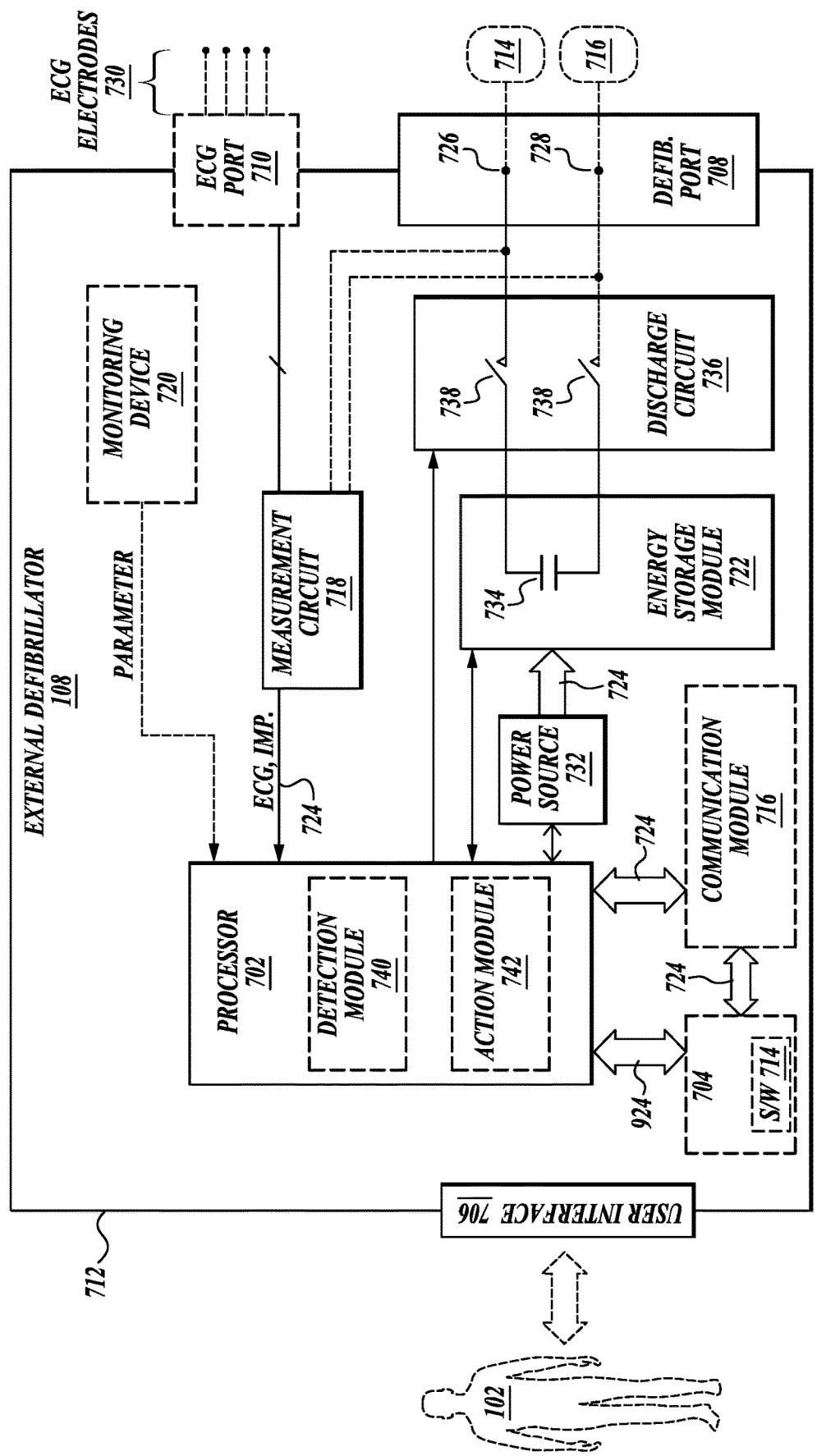
FIG. 7 is a block diagram of an example defibrillator in accordance with one example of the present disclosure.
Figure 8:
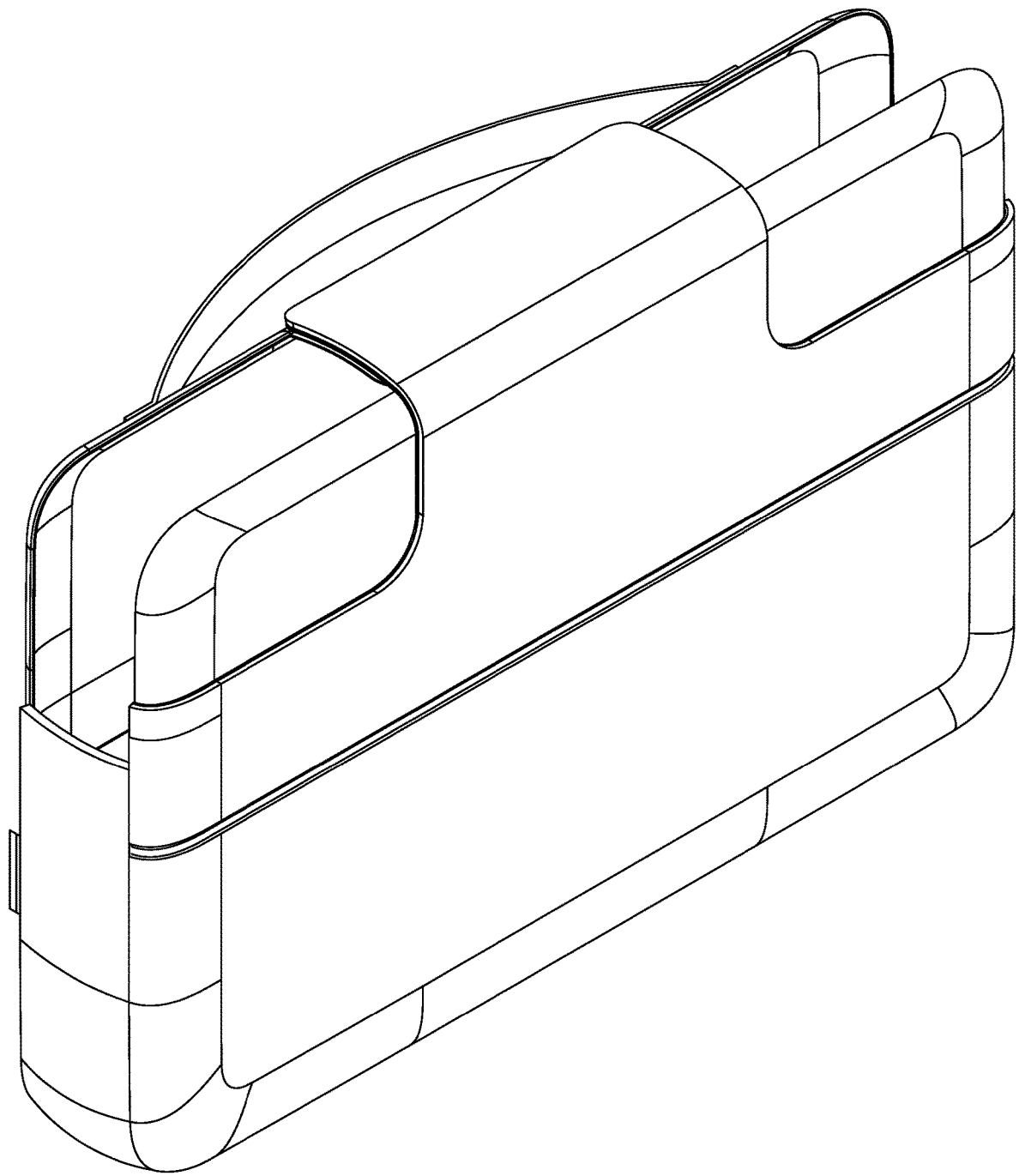
FIG. 8 is a first perspective view of an illustrative embodiment of a carrying case for a patient monitoring medical device.
Figure 9:
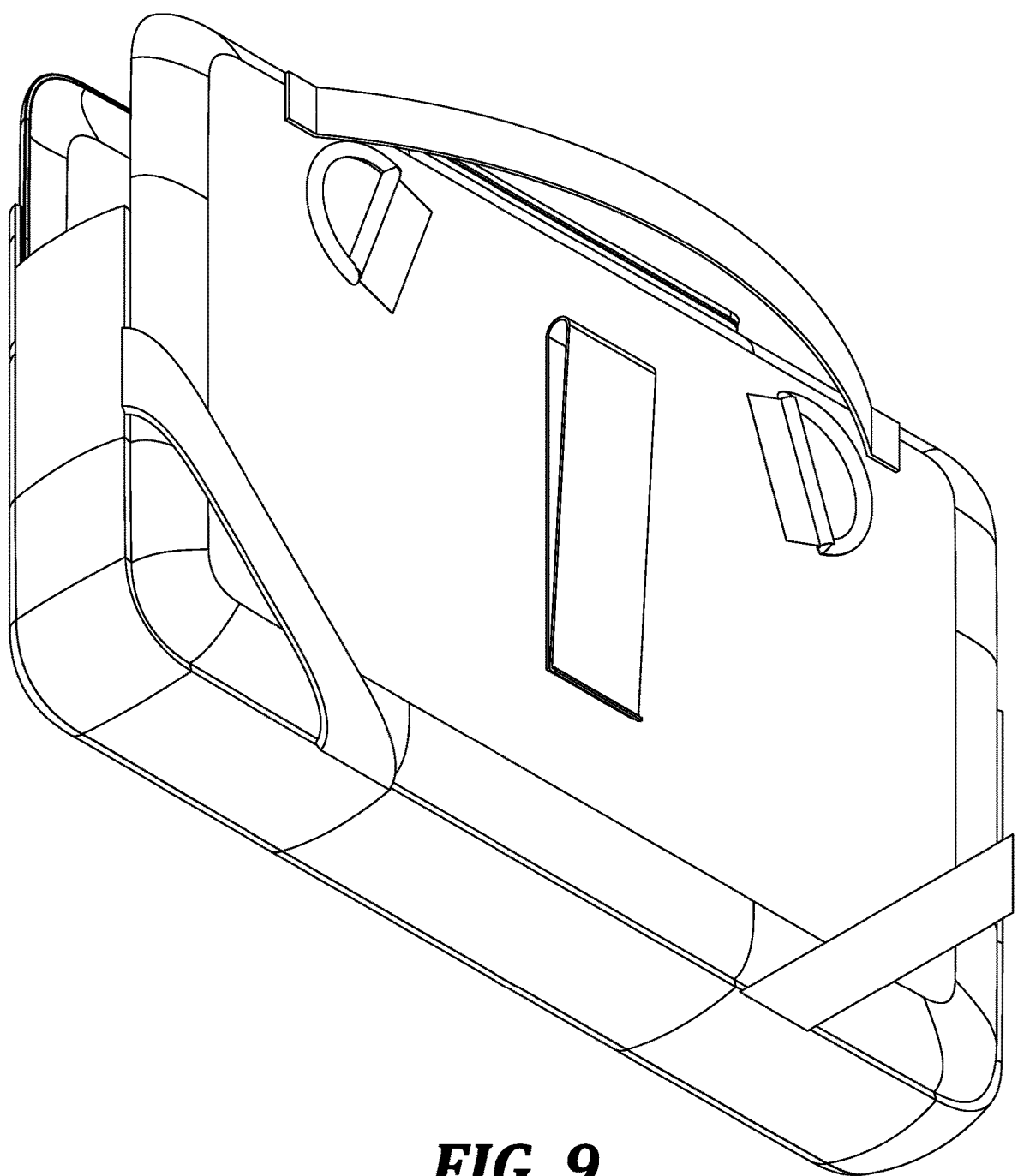
FIG. 9 is a second perspective view of an illustrative embodiment of a carrying case for a patient monitoring medical device.
Figure 10:
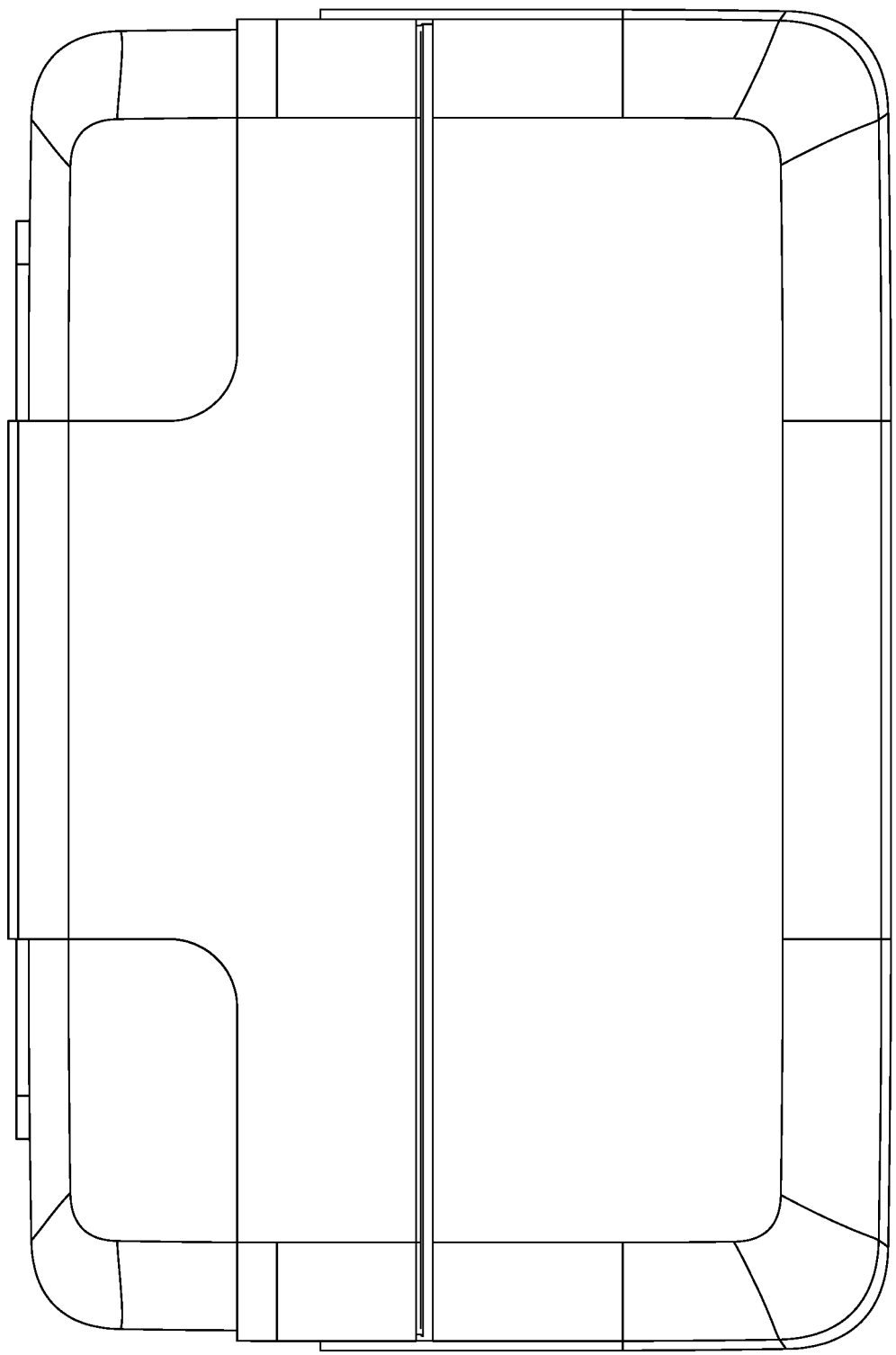
FIG. 10 is a front view of an illustrative embodiment of a carrying case for a patient monitoring medical device.
Figure 11:
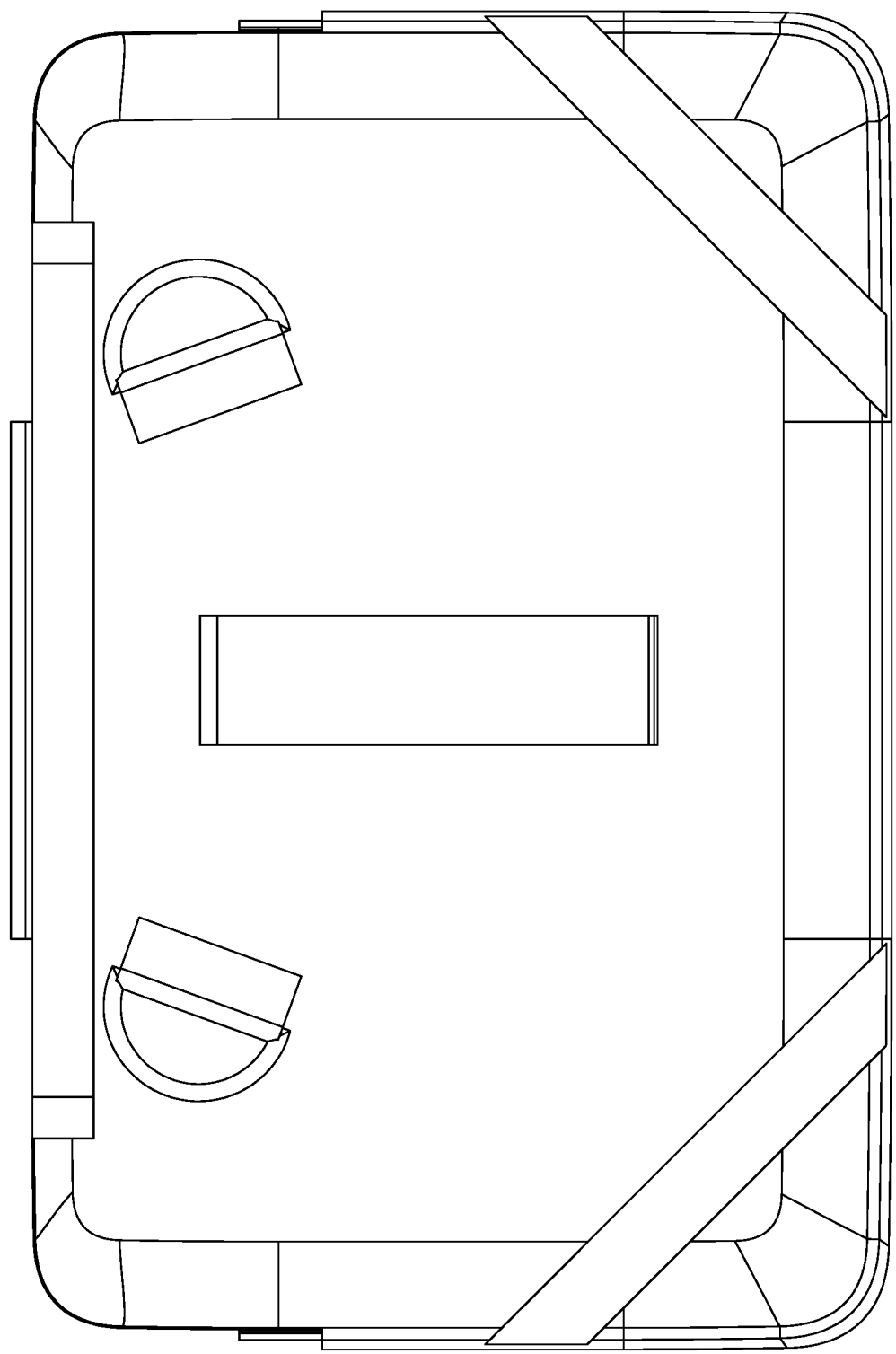
FIG. 11 is a rear view of an illustrative embodiment of a carrying case for a patient monitoring medical device.
Figure 13:
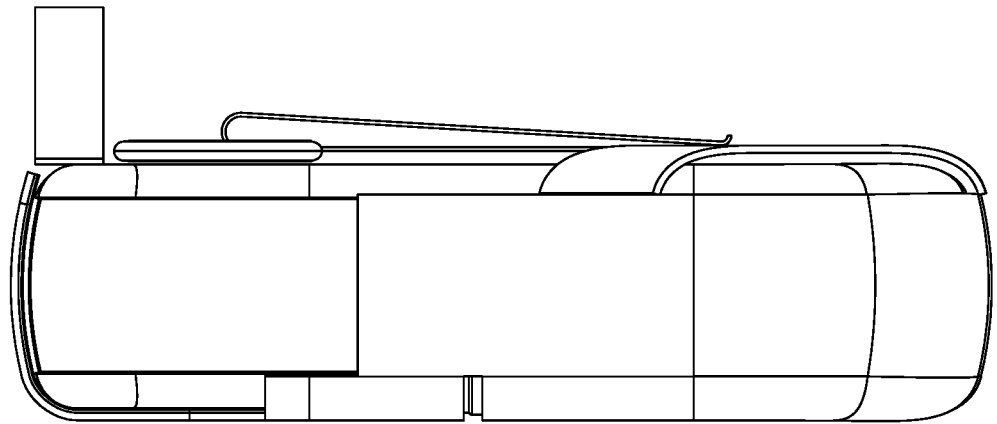
FIG. 13 is a left side view of an illustrative embodiment of a carrying case for a patient monitoring medical device.
Figure 12:
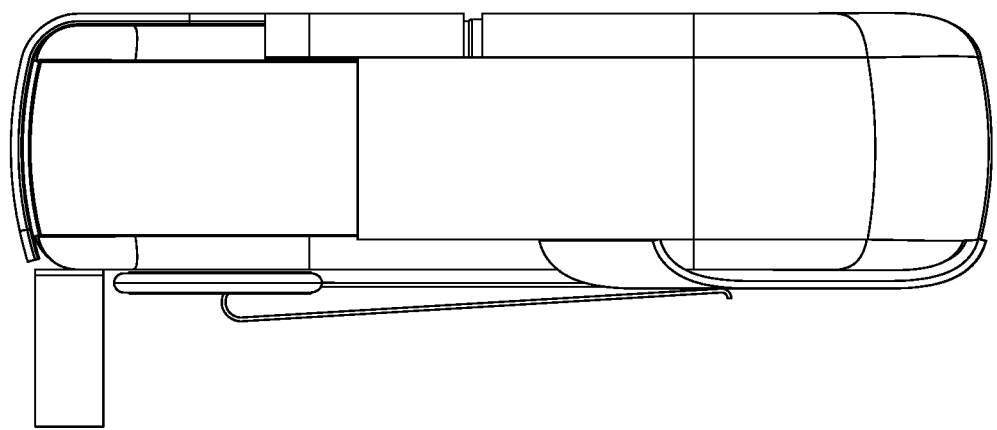
FIG. 12 is a right side of an illustrative embodiment of a carrying case for a patient monitoring medical device.
Figure 14:
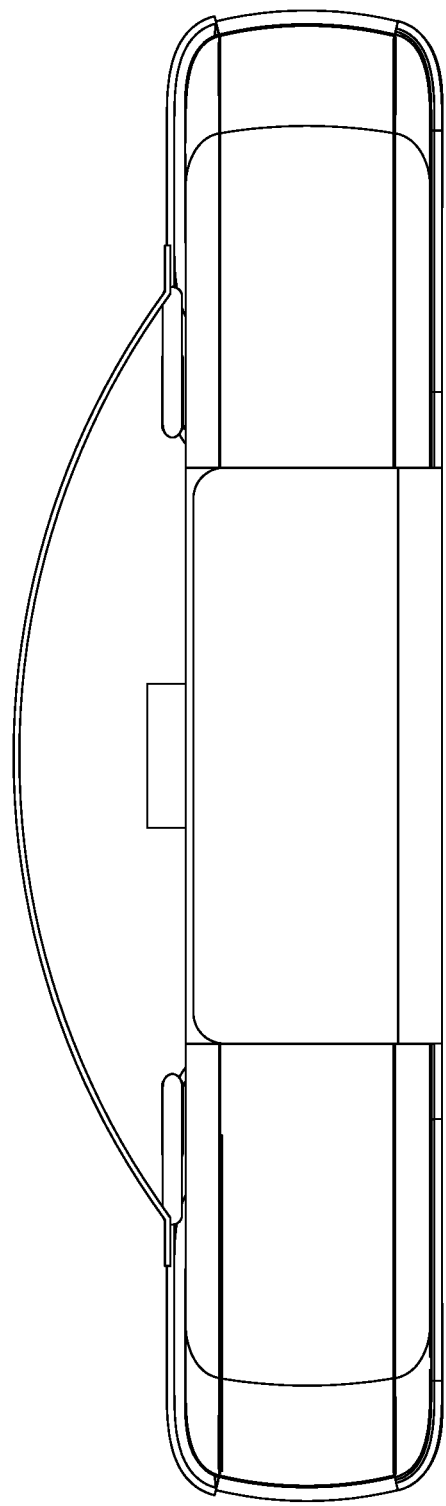
FIG. 14 is a top view of an illustrative embodiment of a carrying case for a patient monitoring medical device.
Figure 15:
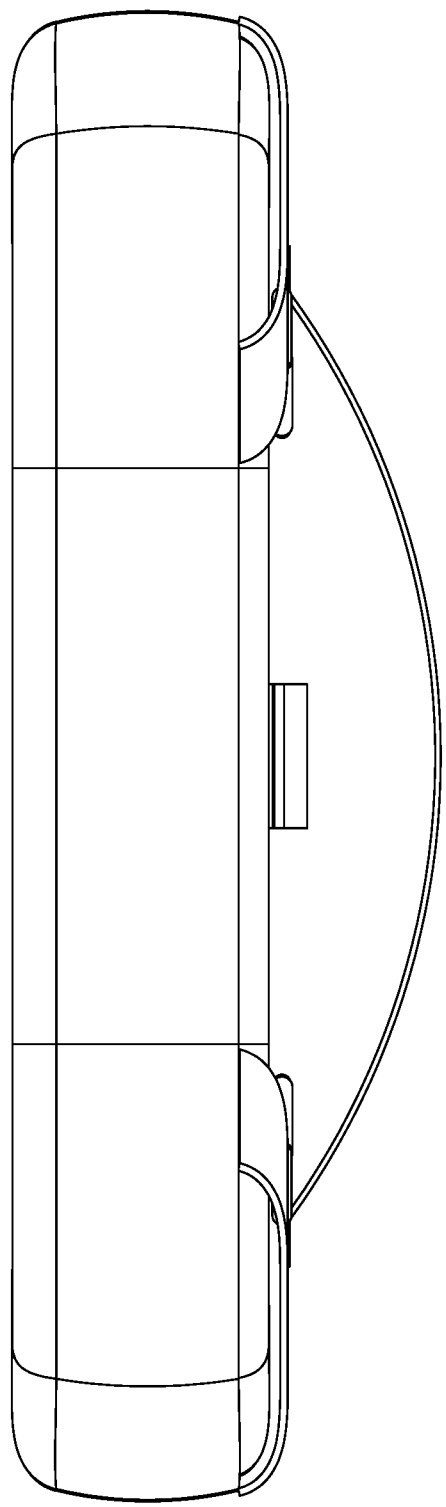
FIG. 15 is a bottom view of an illustrative embodiment of a carrying case for a patient monitoring medical device.

FIG. 7 is a diagram displaying various components of an example external defibrillator 108. The external defibrillator 108 may be an example of the defibrillator 108 described with reference to FIG. 1. The components shown in FIG. 7 may be contained within a single unit or may be separated amongst two or more units in communication with each other. The defibrillator 108 may include a processor 702, memory 704, user interface 706, defibrillation port 708, and ECG port 710, among other components. In some embodiments, the components are contained within a housing 712 or casing. The housing 712 may comprise a hard shell around the components or may comprise a softer shell for increased patient comfort.

The processor 702, memory 704 (including software/firmware code (SW) 714), defibrillation port 708, ECG port 710, communication module 716, measurement circuit 718, monitoring device 720, and energy storage module 722 may communicate, directly or indirectly, with one another via one or more buses 724. The one or more buses 724 may allow data communication between the elements and/or modules of the defibrillator 108.

The memory 704 may include random access memory (RAM), read only memory (ROM), flash RAM, and/or other types. The memory 704 may store computer-readable, computer-executable software/firmware code 714 including instructions that, when executed, cause the processor 702 to perform various functions (e.g., determine shock criteria, determine consciousness of patient, track patient parameters, etc.). In some embodiments, the processor 702 may include an intelligent hardware device, e.g., a central processing unit (CPU), a microcontroller, an application-specific integrated circuit (ASIC), etc.

In some embodiments, the memory 704 can contain, among other things, the Basic Input-Output system (BIOS) which may control basic hardware and/or software operations such interactions and workings of the various components of the defibrillator 108, and in some embodiments, components external to the defibrillator 108. For example, the memory 704 may contain various modules to implement the workings of the defibrillator 108, the WCD system, and other aspects of the present disclosure.

In some embodiments, the defibrillator 108 may include a defibrillation port 708. The defibrillation port 708 may comprise a socket, opening, or electrical connection in the housing 712. In some instances, the defibrillation port 708 may include two or more nodes 726, 728. The two or more nodes 726, 728 may accept two or more defibrillation electrodes (e.g. defibrillation electrodes 114, 116, FIG. 1). The nodes 726, 728 may provide an electrical connection between the defibrillation electrodes 114, 116 and the defibrillator 108. The defibrillation electrodes 114, 116 may plug into the two or more nodes 726, 728 via one or more leads (e.g. leads 118), or, in some instances, the defibrillation electrodes 114, 116 may be hardwired to the nodes 726, 728. Once an electrical connection is established between the defibrillation port 708 and the electrodes 114, 116, the defibrillator 108 may be able to deliver an electric shock to the patient 102.

In some embodiments, the defibrillator 108 may include an ECG port 710 in the housing 712. The ECG port 710 may accept one or more ECG electrodes 730 or ECG leads. In some instances, the ECG electrodes 730 sense a patient's ECG signal. For example, the ECG electrodes 730 may record electrical activity generated by heart muscle depolarization. The ECG electrodes 730 may utilize 7-leads to 12-leads or multichannel ECG, or the like. The ECG electrodes 730 may connect with the patient's skin.

In some embodiments, the defibrillator 108 may include a measurement circuit 718. The measurement circuit 718 may be in communication with the ECG port 710. For example, the measurement circuit 718 may receive physiological signals from ECG port 710. The measurement circuit 718 may additionally or alternatively receive physiological signals via the defibrillation port 708 when defibrillation electrodes 114, 116 are attached to the patient 102. The measurement circuit 718 may determine a patient's ECG signal from a difference in voltage between the defibrillation electrodes 114, 116.

In some embodiments, the measurement circuit 718 may monitor the electrical connection between the defibrillation electrodes 114, 116 and the skin of the patient 102. For example, the measurement circuit 718 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 720 within the housing 712. The monitoring device 720 may monitor at least one local parameter. Local parameters may include physical state of the patient such as ECG, movement, heartrate, pulse, temperature, and the like. Local parameters may also include a parameter of the WCD system (e.g. WCD 104, FIG. 1), defibrillator 108, environmental parameters, or the like.

In some embodiments, the WCD system 104 may include an internal monitoring device 720 and an external monitoring device (e.g. external monitoring device 124). If both monitoring devices 124, 720 are present, the monitoring devices 124, 720 may work together to parse out specific parameters depending on position, location, and other factors. For example, the external monitoring device 124 may monitor environmental parameters while the internal monitoring device 720 may monitor patient and system parameters.

In some embodiments, the defibrillator 108 may include a power source 732. The power source 732 may comprise a battery or battery pack, which may be rechargeable. In some instances, the power source 732 may comprise a series of different batteries to ensure the defibrillator 108 has power. For example, the power source 732 may include a series of rechargeable batteries as a prime power source and a series of non-rechargeable batteries as a secondary source. If the patient 102 is proximate an AC power source, such as when sitting down, sleeping, or the like, the power source 732 may include an AC override wherein the power source 732 draws power from the AC source.

In some embodiments, the defibrillator 108 may include an energy storage module 722. The energy storage module 722 may store electrical energy in preparation or anticipation of providing a sudden discharge of electrical energy to the patient. In some embodiments, the energy storage module 722 may have its own power source and/or battery pack. In other embodiments, the energy storage module 722 may pull power from the power source 732. In still further embodiments, the energy storage module 722 may include one or more capacitors 734. The one or more capacitors 734 may store an electrical charge, which may be administered to the patient. The processor 702 may be communicatively coupled to the energy storage module 722 to trigger the amount and timing of electrical energy to provide to the defibrillation port 708 and, subsequently, the patient.

In some embodiments, the defibrillator 108 may include a discharge circuit 736. The discharge circuit 736 may control the energy stored in the energy storage module 722. For example, the discharge circuit 736 may either electrical couple or decouple the energy storage module 722 to the defibrillation port 708. The discharge circuit 736 may be communicatively coupled to the processor 702 to control when the energy storage module 722 and the defibrillation port 708 should or should not be coupled to either administer or prevent a charge from emitting from the defibrillator 108. In some embodiments, the discharge circuit 736 may include on or more switches 738. The one or more switches 738 may include an H-bridge.

In some embodiments, the processor 702 may execute one or more modules. For example, the processor 702 may execute a detection module 740 and/or an action module 742. The detection module 740 may be a logic device or algorithm to determine if any or a variety thresholds are exceeded which may require action of the defibrillator 108. For example, the detection module 740 may receive and interpret all of the signals from the ECG port 710, the defibrillation port 708, the monitoring device 720, an external monitoring device, and the like. The detection module 740 may process the information to ensure the patient is still conscious and healthy. If any parameter indicates the patient 102 may be experiencing distress or indicating a cardiac episode, the detection module 740 may activate the action module 742.

The action module 742 may receive data from the detection module 740 and perform a series of actions. For example, an episode may merely be a loss of batter power at the power source 732 or the energy storage module 722, or one or more electrodes (e.g., ECG electrodes, defibrillation electrodes) may have lost connection. In such instances, the action module 742 may trigger an alert to the patient or to an outside source of the present situation. If an episode is a health risk, such as a cardiac event, the action module 742 may begin a series of steps. This may include issuing a warning to the patient, issuing a warning to a third party, priming the energy storage module 722 for defibrillation, releasing one or more conductive fluids proximate defibrillation electrodes 114, 116, and the like.

This document may include references to directions, such as "forward," "rearward," "front," "rear," "upward," "downward," "top," "bottom," "right hand," "left hand," "lateral," "medial," "in," "out," "extended," etc. These references, and other similar references, are only to assist in helping describe and to understand the particular embodiments and are not intended to limit the present disclosure to these directions or locations.

The present document may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

While illustrative embodiments have been illustrated and described, it will be appreciated that various changes can be made therein without departing from the spirit and scope of the disclosure.

We claim:

1. A carrying case for a wearable patient monitoring medical device system, comprising:

a container with a front wall, a rear wall, and a gusset that is coupled to the front wall and the rear wall and is operative to separate the front wall from the rear wall to form a first side, a second side, and a bottom of the container, the container being configured to form an opening at a top portion and to receive a housing of a wearable cardioverter defibrillator (WCD), the housing of the WCD having a right side, a left side, a top, and a bottom, each of the first side and the second side of the container being configured to cover a portion of each side of the housing of the WCD and to expose another portion of the respective side of the housing of the WCD, each of the front wall and the rear wall including a plurality of fabric layers;

a latching strap configured to couple the front wall and the rear wall of the container and configured to retain the housing of the WCD in the container the latching strap oriented substantially at a middle of the top of the container configured to provide access to a first portion at the top of the housing of the WCD on the right side and a second portion at the top of the housing of the WCD on the left side;

a pocket formed on the front wall of the container, wherein the pocket has a width substantially equal to the front wall of the container;

connection points inset from an edge of the rear wall, wherein inset of the connection points reduces wobble while the carrying case is worn; and an adjustable strap removably coupled to the connection points, the adjustable strap configured to be worn in various configurations on a body of the patient, wherein the adjustable strap includes a padded portion with a passageway for the adjustable strap to loop through the padded portion, wherein when a patient positions the housing of the WCD in either of a first or second orientation, either the first portion or the second portion of the top of the housing of the WCD remain accessible to the patient, wherein the carrying case is configured to enable while carrying the housing of the WCD: (i) removal of one or more batteries of the housing of the WCD; or (ii) disconnection of a cable from the housing of the WCD without removing the housing of the WCD from the carrying case; or (iii) both (i) and (ii).

2. The carrying case of claim 1, wherein the adjustable strap comprises a first adjustable section and a second adjustable section.

3. The carrying case of claim 1, further comprising:
one or more straps coupled to the rear wall, the straps configured to hold one or more wires.

4. The carrying case of claim 1, further comprising:
a handle coupled to the rear wall.

5. The carrying case of claim 1, further comprising:
one or more strap adjusters coupled to the adjustable strap.

6. The carrying case of claim 5, wherein the one or more strap adjusters have a rubber coating.

7. The carrying case of claim 1, further comprising:
a quick release coupling attached to the adjustable strap.

8. The carrying case of claim 7, wherein the quick release coupling has a rubber coating.

9. The carrying case of claim 1, further comprising:
a belt clip coupled to the back wall.

10. The carrying case of claim 1, wherein the carrying case is structured to be worn on either side of the patient's body, the other portion of the side of the gusset of the container enables a cable to be attached and to exit the carrying case through a rear-facing opening to the back of the patient to be connected to another component of the WCD.

11. The carrying case of claim 10, wherein the first orientation enables a communication screen of the portion of the top of the housing of the WCD to be visible to the patient when the carrying case is worn on one side of the patient and the second orientation enables the communication screen to be visible to the patient when the carrying case is worn on the other side of the patient.

12. The carrying case of claim 1, wherein the gusset separates the front wall from the rear wall on the first side, the second side, and the bottom, wherein the opening of the container is configured to expose a communication screen of the housing of the WCD while the carrying case is worn by the patient.

13. The carrying case of claim 1, further comprising cable management loops configured to retain an excess portion of a cable connected to the housing of the WCD while the housing of the WCD is being carried in the carrying case.

14. The carrying case of claim 1, wherein the padded portion of the adjustable strap is comprised of another plurality of layers, and the passageway for the adjustable strap to loop through is through the top most layer of the another plurality of layers.

15. The carrying case of claim 1, wherein a part of the padded portion of the adjustable strap is retained on a section of the adjustable strap.

16. A wearable cardioverter defibrillator (WCD) system, comprising:
a defibrillator housing having a right side, a left side, a top, and a bottom;
a discharge circuit in communication with the defibrillator housing, the discharge circuit configured to discharge a stored electrical charge through a body of a patient,
a processor within the defibrillator housing, the processor in communication with the discharge circuit; and
a carrying case with a container to hold the defibrillator housing, the carrying case including:
a container with a front wall, a rear wall, and a gusset that is coupled to the front wall and the rear wall and separates the front wall from the rear wall to form a first side, a second side, and a bottom of the container, the container being configured to form an opening at a top portion and to receive the defibrillator housing, each of the first side and the second side of the container being configured to cover each portion of a side of the defibrillator housing and to expose another portion of the respective side of the defibrillator housing, each of the front wall and the rear wall including a plurality fabric layers;
a latching strap configured to couple the front wall and the rear wall of the container and configured to retain the defibrillator housing in the container, the latching strap oriented substantially at a middle of the top of the container configured to provide access to a first portion at the top of the defibrillator housing on the right side and a second portion at the top of the defibrillator housing on the left side;
a pocket formed on the front wall of the container, wherein the pocket has a width substantially equal to the front wall of the container;
connection points inset from an edge of the rear wall, wherein inset of the connection points reduces wobble while the carrying case is worn; and
an adjustable strap removably coupled to the connection points, the adjustable strap configured to be worn in various configurations on a body of the patient, wherein the adjustable strap includes a padded portion with a passageway for the adjustable strap to loop through the padded portion, wherein when a patient positions the defibrillator housing in either of a first or second orientation, either the first portion or the second portion of the top of the defibrillator housing remain accessible to the patient, wherein the carrying case is configured to enable while carrying the housing of the WCD: (i) removal of one or more batteries of the housing of the WCD; or (ii) disconnection of a cable from the housing of the WCD without removing the housing of the WCD from the carrying case; or (iii) both (i) and (ii).

17. The WCD system of claim 16, wherein the adjustable strap comprises a first adjustable section and a second adjustable section.

18. The WCD system of claim 16, further comprising:
one or more straps coupled to the rear wall, the straps configured to hold one or more wires.

19. The WCD system of claim 16, further comprising:
a handle coupled to the rear wall.

20. The WCD system of claim 16, furthering comprising:
one or more strap adjusters coupled to the adjustable strap.

21. The WCD system of claim 16, further comprising:
a quick release coupling attached to the strap.

22. A carrying case for a wearable cardioverter defibrillator (WCD), comprising:
a container with a front wall, a rear wall, and a gusset that is coupled to the front wall and the rear wall and separates the front wall from the rear wall to form a first side, a second side, and a bottom of the container, the container being configured to form an opening at a top portion and to receive a housing of the WCD, the housing of the WCD having a right side, a left side, a top, and a bottom, each of the first side and the second side of the gusset being configured to cover a portion of each side of the housing of the WCD and to expose another portion of the respective side of the housing of the WCD, each of the front wall and the rear wall including a plurality of fabric layers;

a latching strap configured to couple the front wall and the rear wall of the container and configured to retain the housing of the WCD in the container, the latching strap oriented substantially at a middle of the top of the container configured to provide access to a portion of the top of the housing of the WCD at both the right side and the left side of the housing of the WCD;

connection points inset from an edge of the rear wall, wherein inset of the connection points reduces wobble while the carrying case is worn;

an adjustable strap removably coupled to the connection points, the adjustable strap configured to be worn in various configurations on a body of the patient, wherein the adjustable strap includes a padded portion with a passageway for the adjustable strap to loop through the padded portion;

a pocket formed on the front wall of the container, wherein the pocket has a width substantially equal to the front wall of the container;

one or more straps coupled to the rear wall, the straps configured to hold one or more wires;

one or more strap adjusters coupled to the strap; and a quick release coupling attached to the strap, wherein when a patient positions the housing of the WCD in either of a first or second orientation, the portions of the top of the housing of the WCD remain accessible to the patient, and wherein the carrying case is configured to enable while carrying the housing of the WCD: (i) removal of one or more batteries of the housing of the WCD; or (ii) disconnection of a cable from the housing of the WCD without removing the housing of the WCD from the carrying case; or (iii) both (i) and (ii).

\* \* \* \* \*